(12) United States Patent
Panzenbeck

(10) Patent No.: US 11,033,248 B2
(45) Date of Patent: Jun. 15, 2021

(54) ORIENTATION PINS FOR DEVICE USING RADIAL ULTRASOUND

(71) Applicant: Spriation Inc., Redmond, WA (US)

(72) Inventor: Jason T. Panzenbeck, Redmond, WA (US)

(73) Assignee: GYRUS ACMI, INC., Westborough, MA (US)

( * ) Notice: Subject to any disclaimer, the term of this patent is extended or adjusted under 35 U.S.C. 154(b) by 531 days.

(21) Appl. No.: 15/908,392

(22) Filed: Feb. 28, 2018

(65) Prior Publication Data
US 2019/0261946 A1 Aug. 29, 2019

(51) Int. Cl.
| | |
|---|---|
| *A61B 8/00* | (2006.01) |
| *A61B 8/12* | (2006.01) |
| *A61B 1/00* | (2006.01) |
| *A61B 8/08* | (2006.01) |

(52) U.S. Cl.
CPC .......... *A61B 8/445* (2013.01); *A61B 1/00154* (2013.01); *A61B 8/0891* (2013.01); *A61B 8/12* (2013.01); *A61B 8/461* (2013.01); *A61B 8/54* (2013.01); *A61B 8/4494* (2013.01); *A61B 8/468* (2013.01)

(58) Field of Classification Search
CPC ........... A61B 8/445; A61B 5/54; A61B 8/461; A61B 8/0891; A61B 8/12; A61B 1/00154; A61B 8/4494; A61B 8/468; A61B 1/00098; A61B 1/018; A61B 8/00; A61M 2025/0036; A61M 25/0108; A61M 25/003; A61M 25/0105
See application file for complete search history.

(56) References Cited

U.S. PATENT DOCUMENTS

| | | | |
|---|---|---|---|
| 5,899,882 A * | 5/1999 | Waksman | A61M 25/1002 604/103.07 |
| 6,283,951 B1 | 9/2001 | Flaherty | |
| 6,302,875 B1 | 10/2001 | Makower et al. | |
| 6,544,230 B1 * | 4/2003 | Flaherty | A61B 17/22 604/164.09 |
| 6,942,680 B2 | 9/2005 | Grayzel | |
| 9,955,994 B2 | 5/2018 | Nita et al. | |

(Continued)

FOREIGN PATENT DOCUMENTS

| | | |
|---|---|---|
| WO | WO2005023336 A2 | 3/2005 |
| WO | WO2012014860 A1 | 9/2013 |

*Primary Examiner* — Sanjay Cattungal
(74) *Attorney, Agent, or Firm* — Clements Bernard Walker; Michael S. Smith

(57) ABSTRACT

A system for determining orientation of a distal end of a catheter. The system includes a flexible shaft having a first lumen, a second lumen, a third lumen, a fourth lumen, a first orientation pin and a second orientation pin. The first orientation pin is received within the third lumen and the second orientation pin is received within the fourth lumen. The flexible shaft includes a cross-sectional dimension and the third lumen and the fourth lumen include longitudinal axes that are located on the same half of the cross-sectional dimension of the catheter. The second lumen includes an exit port for exposing at least a portion of the second lumen of the cap portion and a ramp. A distal end of the flexible shaft is made of material permeable to ultrasound signals and the orientation pins include one or more materials that are non-permeable to ultrasound signals.

12 Claims, 12 Drawing Sheets

(56) References Cited

U.S. PATENT DOCUMENTS

| | | | |
|---|---|---|---|
| 2002/0156521 A1* | 10/2002 | Ryan | A61F 2/07 623/1.13 |
| 2008/0154345 A1* | 6/2008 | Taylor | A61B 1/3137 607/93 |
| 2009/0005757 A1* | 1/2009 | Taber | A61M 25/01 604/523 |
| 2014/0135576 A1* | 5/2014 | Hebert | A61B 1/0055 600/109 |
| 2016/0220302 A1* | 8/2016 | Zarins | A61B 18/1482 |
| 2016/0279388 A1* | 9/2016 | Barrish | A61B 34/20 |
| 2018/0028787 A1* | 2/2018 | McNiven | A61F 2/24 |
| 2018/0049759 A1 | 2/2018 | Thomas | |

* cited by examiner

ORIENTATION PINS FOR DEVICE USING RADIAL ULTRASOUND

BACKGROUND

The statements in this section merely provide background information related to the present disclosure and may not constitute prior art.

The tools that are currently available for the ultrasound visualization and sampling of peripheral lung tumors are limited in their range of motion and diagnostic capabilities. Typically, during peripheral sampling a guide sheath is fed through a bronchoscope and extended so far beyond the reach of the bronchoscope that the distal end of the guide sheath is not visible. A radial endobronchial ultrasound (EBUS) miniprobe is then threaded through the guide sheath and used to determine the approximate location of the tumor.

Unfortunately, a peripheral tumor that is located off to one side of an airway (as opposed to one that is centered around an airway) has a substantially lower diagnostic yield in part due to the limitations of current radial EBUS technology, which allows the operator to discern the depth from the probe, but not the direction of the tumor. A sampling needle that extends off-axis from the length of the catheter and, therefore, requires a knowledge of rotational orientation of the needle and the sampling target. The radial ultrasound probe does not show the orientation of the needle to the lesion. The radial ultrasound image is a 360° image that allows the user to see a lesion, however, the user cannot tell if the needle is pointing towards the lesion.

SUMMARY

The present invention provides an improved guide sheath for use with a medical scope, such as a bronchoscope. The present invention uses echogenic orientation pins that are attached to a catheter device. The orientation pins are visible on an ultrasound image, thus alerting the user to the rotational orientation of a medical device passed through the catheter device. When the ultrasound probe visualizes a target, the ultrasound probe image also shows the orientation pins alerting the user to the direction the medical device will protrude. If the medical device will protrude in the wrong direction, the user can rotate the catheter device until the orientation pins, and thus the medical device, point towards the target.

Accordingly, pursuant to one aspect of the present invention, an example system includes a flexible catheter portion having a first lumen, a second lumen, a third lumen, a fourth lumen, a first orientation pin and a second orientation pin. The first orientation pin is received within the third lumen and the second orientation pin is received within the fourth lumen.

In still another aspect of the invention, the system further includes a cap portion. The first and second lumens are included within the catheter portion. The cap portion includes the first lumen, the second lumen, the third lumen, and the fourth lumen. The first orientation pin is received within the third lumen of the cap portion and the second orientation pin is received within the fourth lumen of the cap portion.

In further aspects of the invention, the cap portion includes a cross-sectional dimension. The third lumen and the fourth lumen of the cap portion include longitudinal axes that are located on the same half of the cross-sectional dimension of the cap portion. The second lumens of the flexible catheter portion and the cap portion are located on the same half of the cross-sectional dimension as the third and fourth lumens of the catheter portion and the cap portion.

In still other aspects of the invention, the cap portion further includes an exit port for exposing at least a portion of the second lumen of the cap portion and a ramp located at a distal end of the second lumen of the cap portion.

In yet other aspects of the invention, the cap portion includes one or more materials that are permeable to ultrasound signals and the orientation pins include one or more materials that are non-permeable to ultrasound signals. The orientation pins also include one or more echogenic features, such as laser scribes, divots, holes, etc.

In further aspects of the invention, three or more orientation pins may be used. For example, a third orientation pin may be located adjacent to one of the other pins, thus producing an ultrasound image that easily allows one to quickly understand rotational direction to a target.

Further features, advantages, and areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely exemplary in nature and is not intended to limit the present disclosure, application, or uses.

Figure 1:
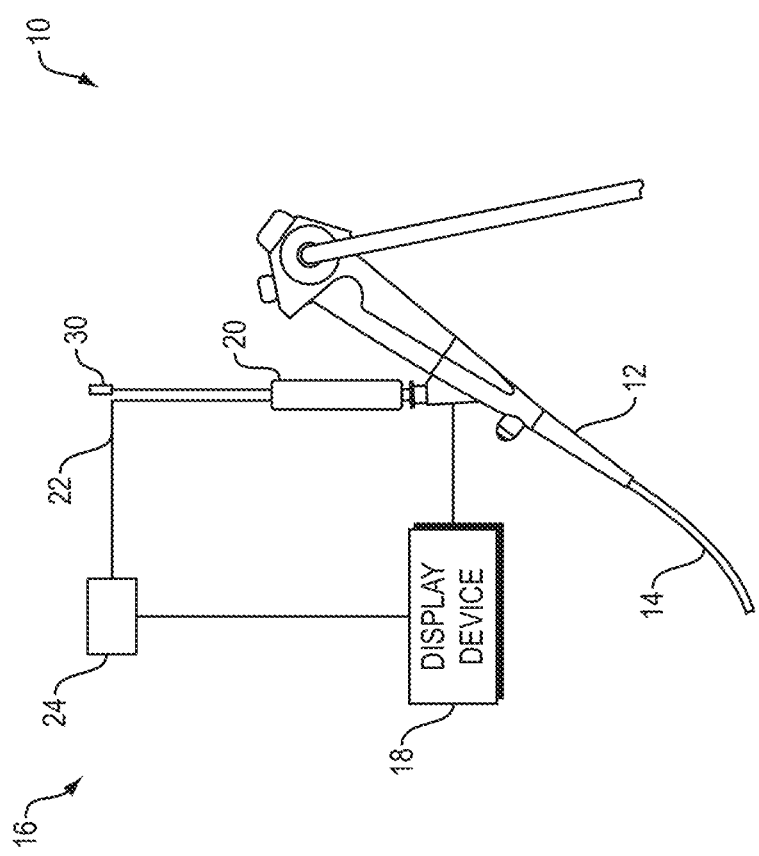
FIG. 1 illustrates an example of a bronchoscope system formed in accordance with an embodiment of the present invention.
Figure 2A:
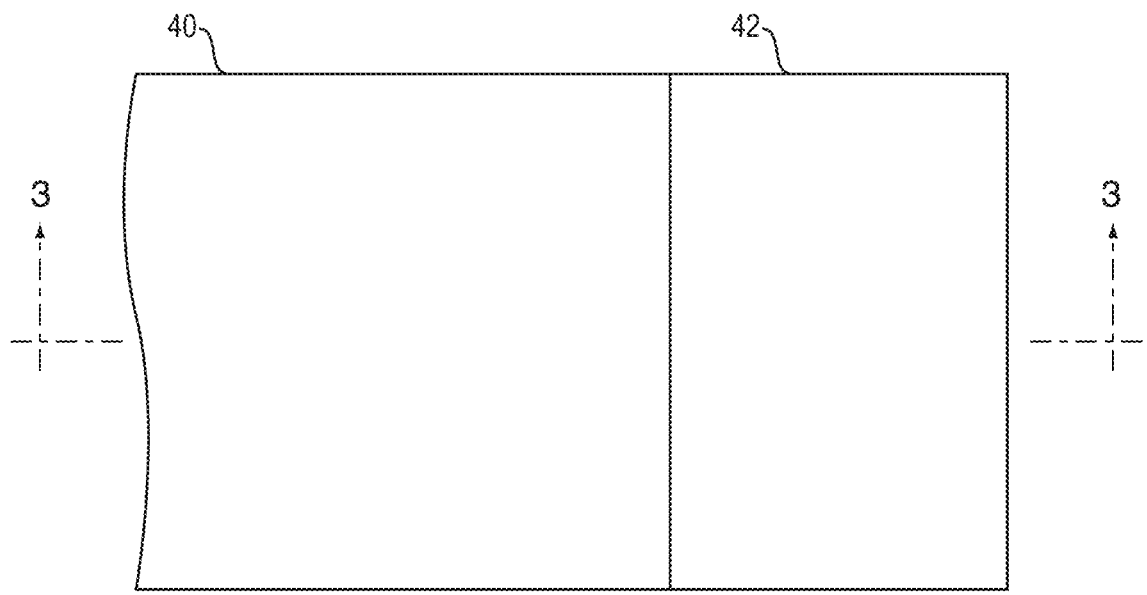
FIG. 2A is a side view of a distal end of a device formed in accordance with an embodiment of the present invention.
Figure 2B:
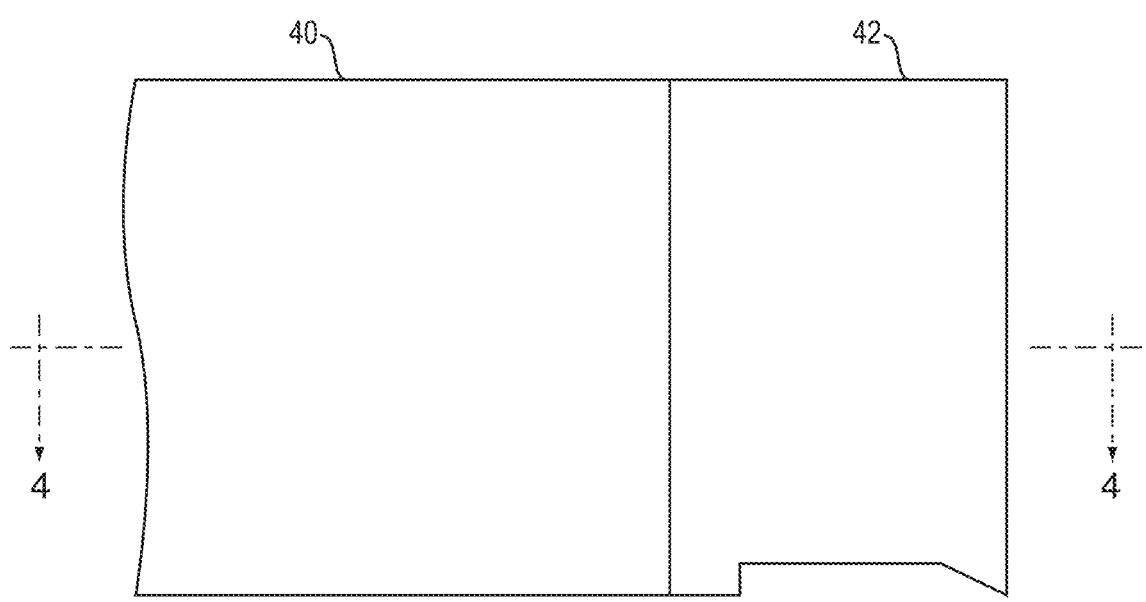
FIG. 2B is a side view of a distal end of the device of FIG. 2A rotated 90° about a longitudinal dimension.
Figure 3:
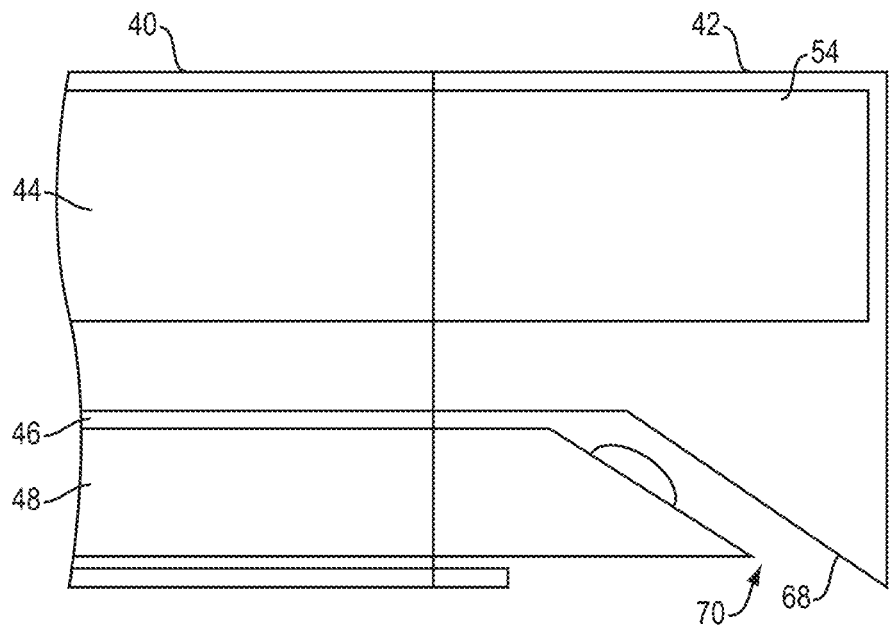
FIG. 3 is a cross-sectional view of a portion of the device shown in FIG. 2A.
Figure 4:
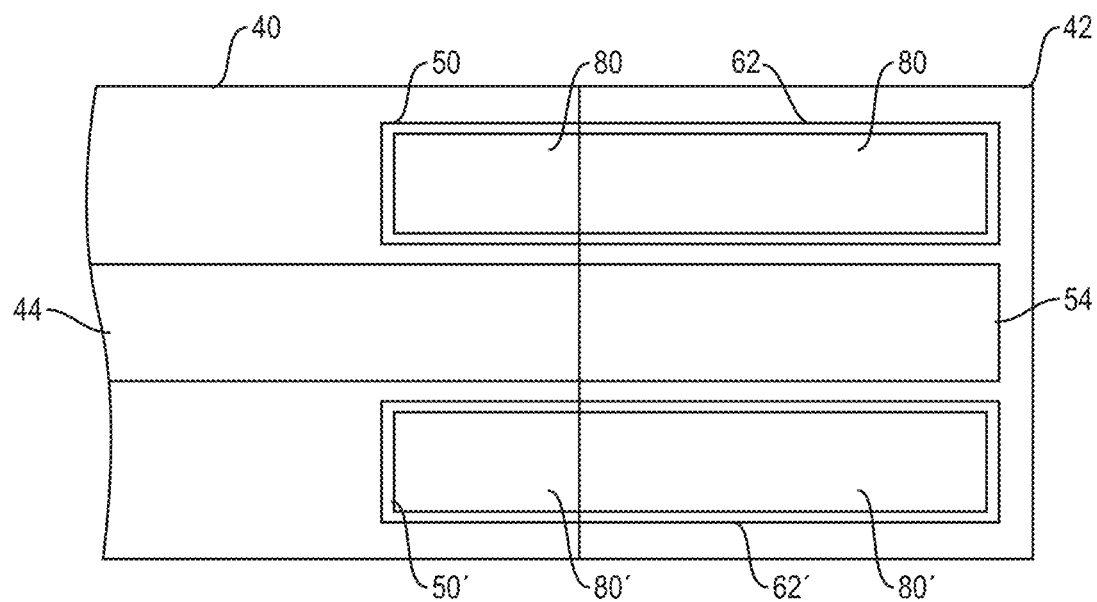
FIG. 4 is a cross-sectional view of a portion of the device shown in FIG. 2B.
Figure 5:
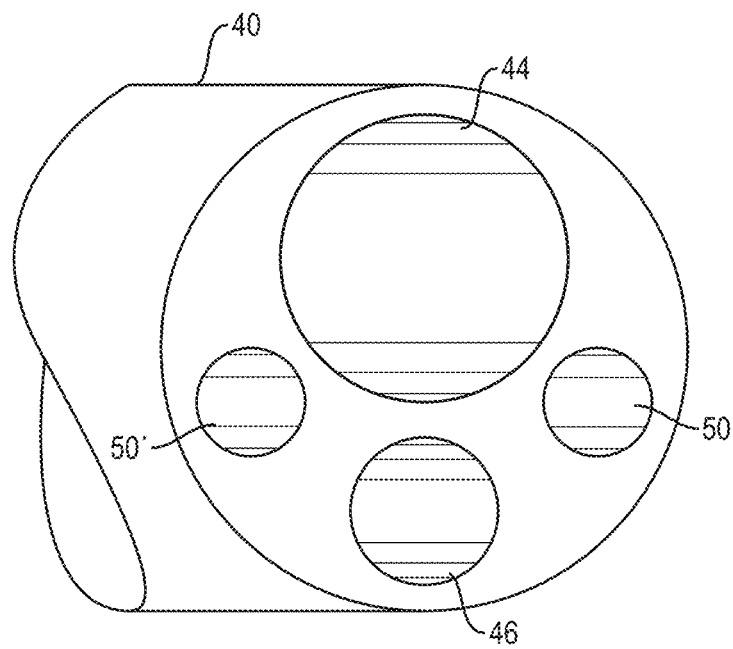
FIG. 5 is a perspective view of a portion of a distal end of a main catheter section of the device of FIG. 2A.

Referring now to FIG. 1, a bronchoscope system 10 includes a bronchoscope 12 with an insertion tube 14, a radial ultrasound system 16 and an access device 20. The radial ultrasound system 16 includes a signal processor 24, a display device 18 and a radial ultrasound probe 22. The radial ultrasound probe 22 and a medical device 30, such as a needle for sampling and/or medicant delivery, are received within the bronchoscope 12 via a handle component of the access device 20.

The display device 18 is in wired or wireless signal communication with the bronchoscope 12 and/or the signal processor 24. The display device 18 presents images generated based on information received from the bronchoscope 12 and/or the signal processor 24 that receives image information from a radial ultrasound transducer at the distal end of the radial ultrasound probe 22. A diagnostic bronchoscope (e.g., BF-X190 produced by Olympus®) is an example of the bronchoscope 12 and the radial endobronchial ultrasound (EBUS) miniprobes produced by Olympus® are examples of the radial ultrasound device 16.

The present invention uses echogenic orientation pins that are attached to the torqueable insertion device. The orientation pins are visible on the ultrasound image and thus alert the user to the rotational orientation of the distal end of the access device 20 and the needle relative to a target.

Figure 6:
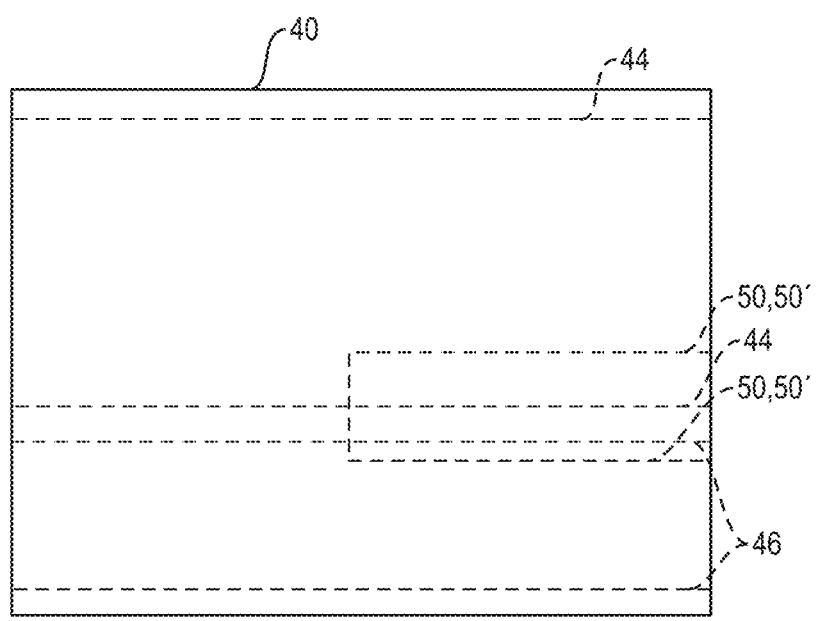
FIG. 6 is a side, x-ray view of the distal end of the main catheter section of FIG. 5.
Figure 7:
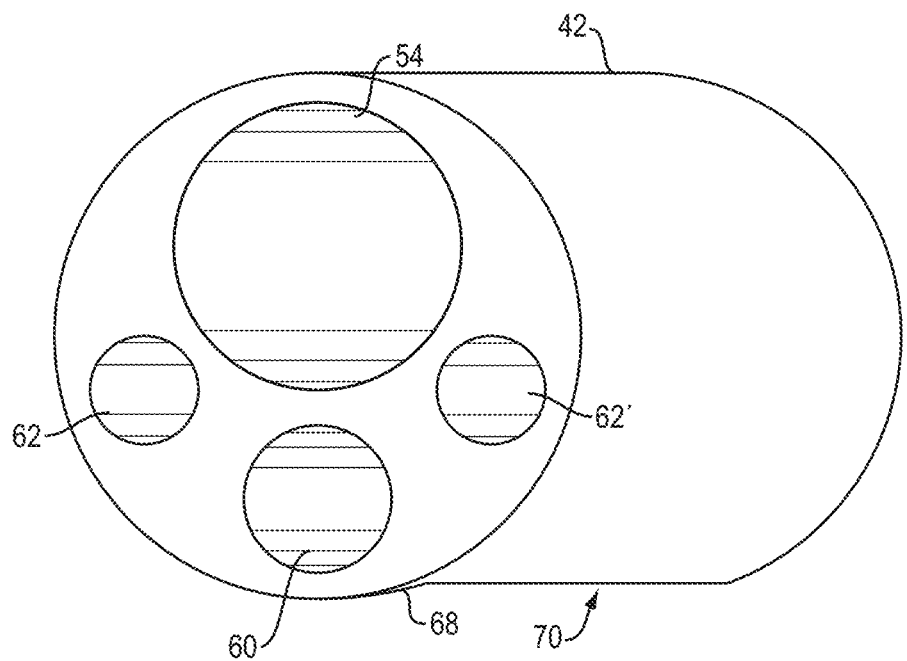
FIG. 7 is a perspective view of a proximal end of a cap section of the device of FIG. 2A.
Figure 8:
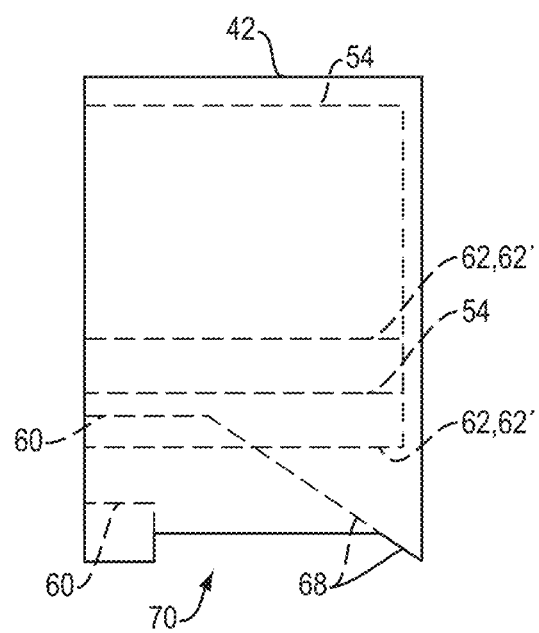
FIG. 8 is a side, x-ray view of the cap section of FIG. 7.

FIGS. 2-8 show an example of a distal end of the access device 20. The access device 20 includes a catheter portion 40 and a cap portion 42 at a distal end of the catheter portion 40. The catheter portion 40 extends from a handle portion (not shown). The catheter portion 40 includes a radial ultrasound lumen 44, a second lumen 46, a third lumen 50 and a fourth lumen 50'. The lumens 44, 46, 50, 50' are all accessible via a distal face of the catheter portion 40. The lumens 44, 46 extend to proximal ports (not shown) located at the handle portion, a port on a handle of the bronchoscope or other scope device, or at a position accessible by an operator. The lumens 44, 46 allow devices to be inserted from the proximal ends all the way to the distal end of the catheter portion 40. The radial ultrasound lumen 44 is sized to slidably receive a radial ultrasound probe (not shown). The second lumen 46 is sized to receive a medical device 48, such as a needle. In one embodiment, the third and fourth lumens 50, 50' extend only a predefined distance from the distal end of the catheter portion 40 (FIG. 6).

As shown in FIGS. 3, 4, 7 and 8, the cap portion 42 includes a first lumen 54, a second lumen 60, a third lumen 62 and a fourth lumen 62'. A first orientation pin 80 and a second orientation pin 80' each include a proximal end and a distal end. The proximal ends of the pins 80 and 80' are at least partially received within the third and fourth lumens 50 and 50' of the catheter portion 40. The distal ends of the pins 80, 80' are at least partially received within the third and fourth lumens 62, 62' of the cap portion 42. The pins 80, 80' may be pressure fitted into the lumens 50, 50', 62, 62' and/or are attached to one or more of the lumens 50, 50', 62, 62' with a reflow process, an adhesive or a welded joint. The pins 80, 80' may have a variety of shapes, such as round, oval, rectangular, with the lumens 50, 50', 62, 62' having comparable shapes. In one embodiment, the pin 80 is a different shape than the pin 80' with the lumens 50, 50', 62, 62' having corresponding shapes. The pins 80, 80' may include metal (e.g., stainless steel) or another material having ultrasound reflective properties. The pins 80, 80' may include reflective features, such as etchings or grooves, for increasing the echogenicity of the pins 80, 80'.

In one embodiment, the catheter is made of a braided (stainless steel) sheath with PTFE liners in the lumens and Pebax making up the body and the outer jacket. The cap may be made out of polycarbonate, PEEK, Ultem, or TPX (polymethylpentene).

In one embodiment, at least a proximal portion of the cap portion 42 is sized to be received within slots at the distal end of the catheter portion 40 or is sized to receive the distal end of the catheter portion 40, such that the pins 80, 80' are received within the third and fourth lumens 62, 62' and the first lumen 54 lines up with the radial ultrasound lumen 44 and the second lumen 60 lines up with the second lumen 46 of the catheter portion 40. Other methods of temporarily or permanently attaching the cap portion 42 to the distal end of the catheter portion 40 may be used. The distal end of the second lumen 60 of the cap portion 42 includes a side port 70 and a ramp 68. The ramp 68 causes the medical device 48 to deflect and exit the cap portion 42 through the side port 70. The lumens 54, 62, 62' may be closed/sealed or opened at their distal ends.

When a radial ultrasound probe is positioned within the cap portion 42, the radial ultrasound probe is able to produce a 360° image. The 360° image includes reflections of the orientation pins 80, 80'. Because the orientation pins 80, 80' are located on the same half of the first lumen 54, then any medical device passed through the second lumen 60 and out the side port 70 will interact with tissue visually located on the 360° image between the shortest arced distance between the reflections of the orientation pins 80, 80'. This is show by the example image of FIG. 9.

Figure 9:
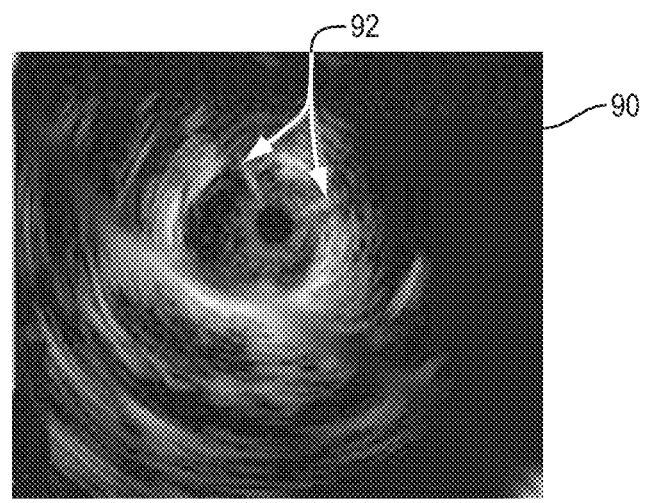
FIG. 9 is an exemplary image generated by a radial ultrasound probe used with the components shown in FIGS. 2-8.
Figure 10:
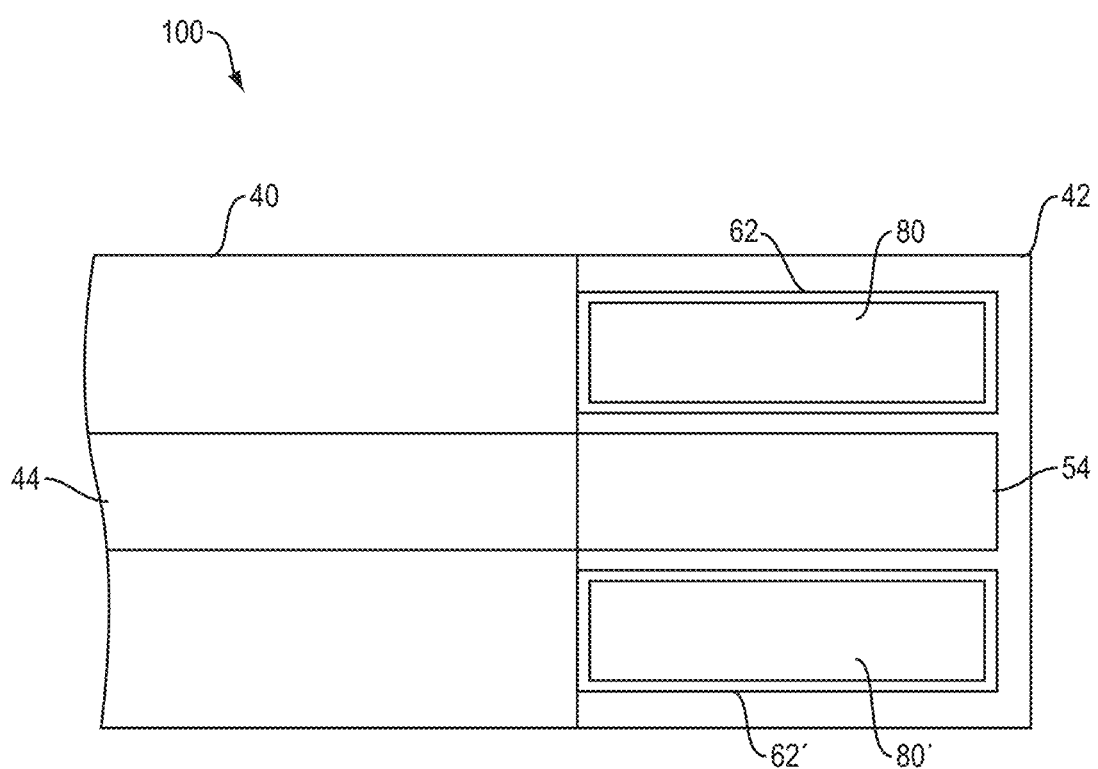
FIG. 10 is a cross-sectional view of a main catheter and cap formed in accordance with an embodiment of the present invention.
Figure 11:
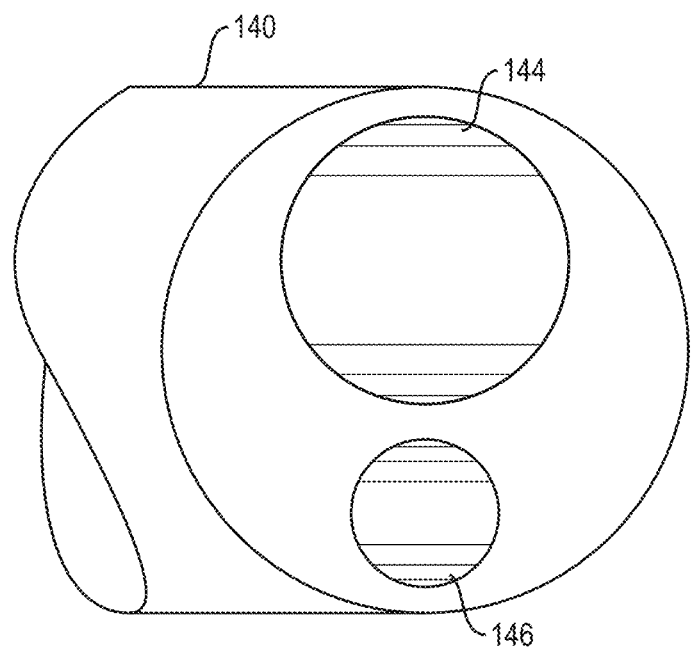
FIG. 11 is a perspective view of a portion of a distal end of a main catheter section of the device of FIG. 10.
Figure 12:
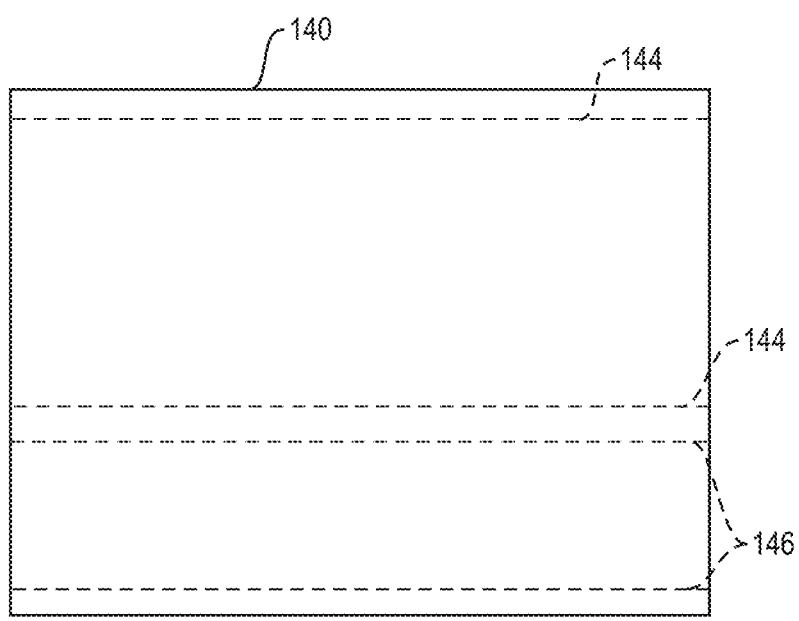
FIG. 12 is a side, x-ray view of the distal end of the main catheter section of FIG. 10.
Figure 13:
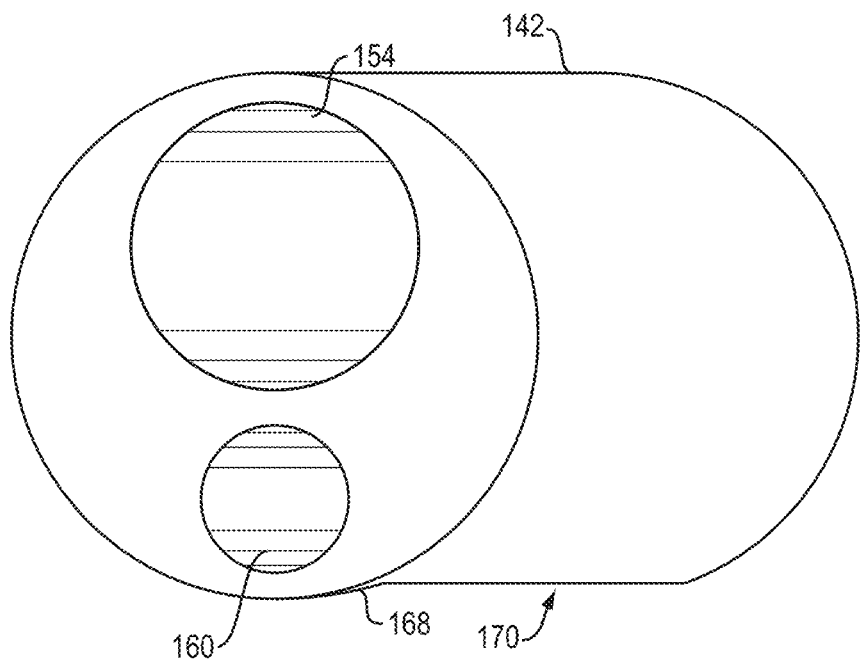
FIG. 13 is a perspective view of a proximal end of a cap section of the device of FIG. 10.
Figure 14:
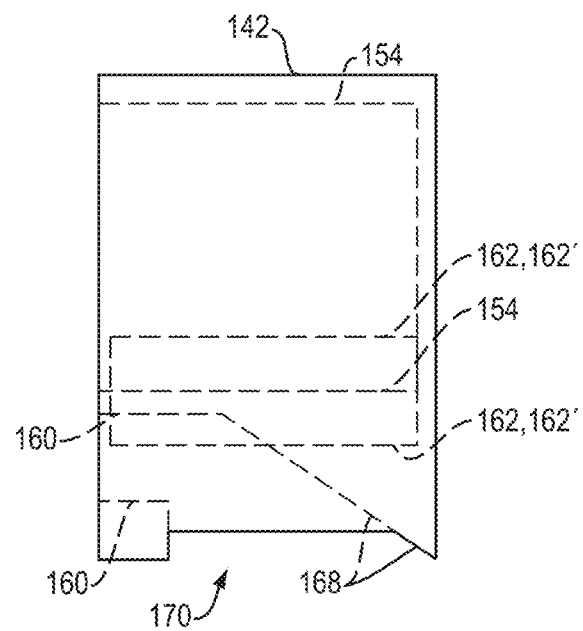
FIG. 14 is a side, x-ray view of the cap section of FIG. 10.

FIG. 9 illustrates an image 90 outputted to the display device 18. The image 90 is generated by the radial ultrasound system 16 when the insertion tube 14 with an ultrasound transducer received at the distal end are positioned within a body lumen. The image 90 shows an image with 360° of imaging features. The image 90 also includes feedback 92 identifying the orientation pins. The side port 70 is located between the orientation pins 80, 80' where the arc between the pins 80, 80' is the smallest. Thus, a user will know that any medical device exiting the side port 70 will always exit at about this smallest arc location. In the image 90, the medical device will exit the side port 70 between approximate angular values 350° to 80°. In the image 90, 000° would be at the 12 o'clock position. Therefore, if a target is identified in a radial ultrasound image, all the user needs to do in order to have the medical device interact with that target is to rotate the catheter portion 40 until the target is located within a smallest pie of the 360° image that is bordered by the orientation pins feedback 92.

As shown in FIGS. 10-14, orientation pins 180, 180' are only included in a cap section 142 and no orientation pin lumens are included in a catheter portion 140.

Figure 15:
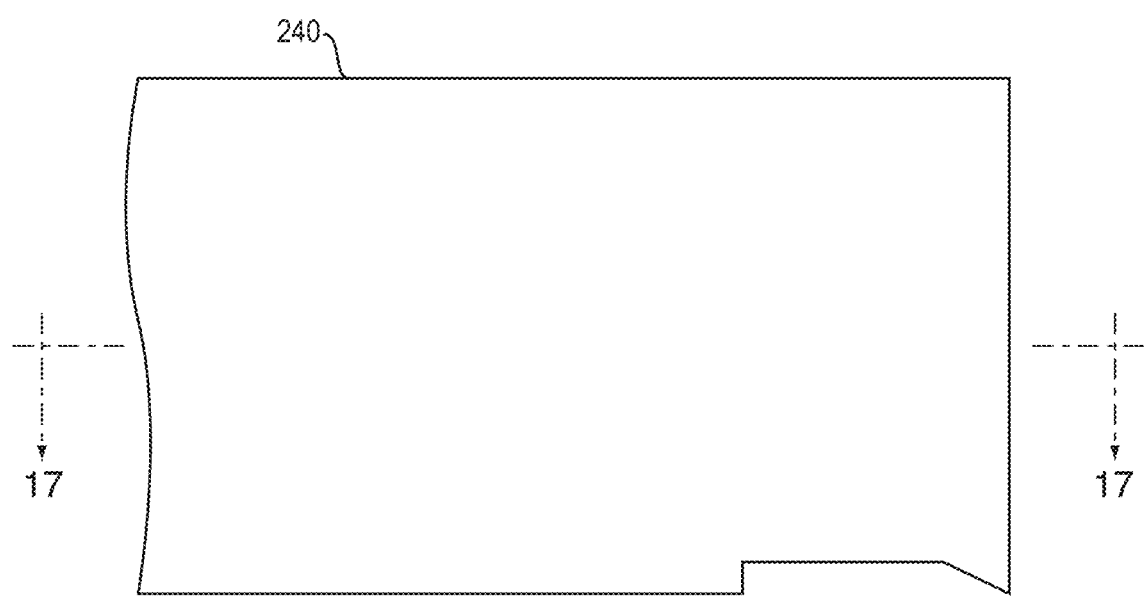
FIG. 15 is a side view of a distal end of a device formed in accordance with an embodiment of the present invention.
Figure 16:
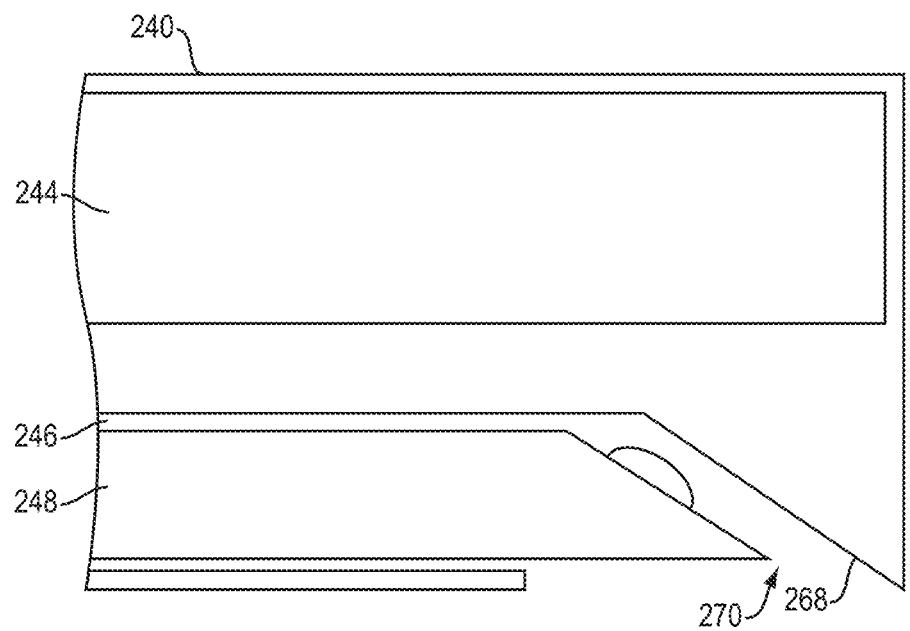
FIG. 16 is a cross-sectional view of a portion of the device shown in FIG. 15.
Figure 17:
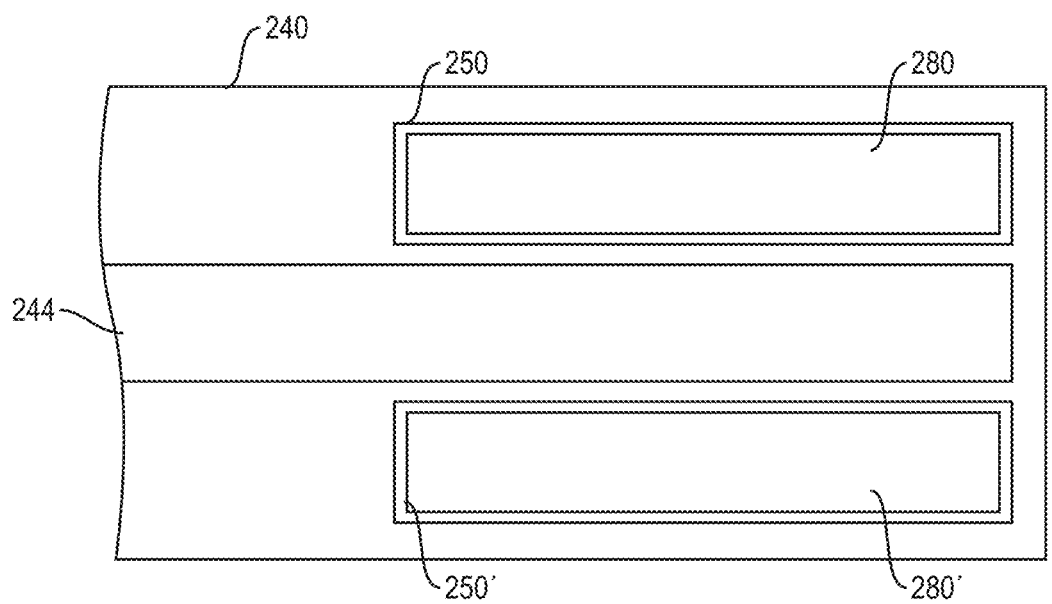
FIG. 17 is a cross-sectional view rotated 90° of the portion of the device shown in FIG. 15.

As shown in FIGS. 15-17, a catheter portion 240 does not include a cap portion. The catheter portion 240 includes at least all the features of the cap devices 42, 142 described above and features shown in the following features.

Figure 18:
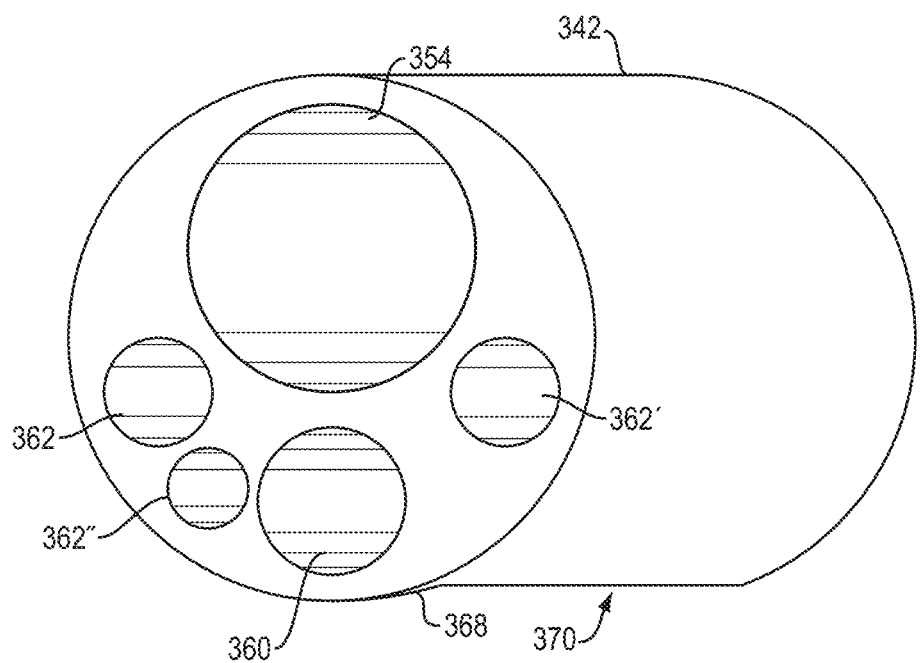
FIG. 18 is a cross-sectional, perspective view of a proximal end of a cap section of the device of FIG. 2A.
Figure 19:
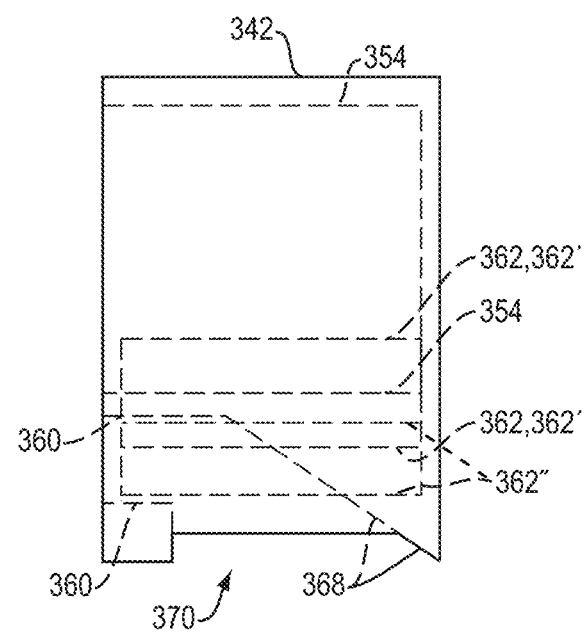
FIG. 19 is a side, x-ray view of the cap section of FIG. 18.

As shown in FIGS. 18 and 19, three orientation pins are use. Two pins are located in pin lumens 362, 362" adjacent to one another on one half of a catheter 342 and a third pin is located in a pin lumen 362' on the other half of the catheter 342. In one embodiment, the three pin lumens 362, 362', 362" may be located in the cap portion, a single catheter or both.

Any of the lumens described above may be exposed at their proximal or distal ends.

EMBODIMENTS

A. A catheter system comprising: a flexible shaft comprising: a first lumen; a second lumen; a third lumen; a fourth lumen; a first orientation pin; and a second orientation pin, wherein the first orientation pin is received within the third lumen and the second orientation pin is received within the fourth lumen.

B. The system of A, wherein the flexible shaft comprises a cross-sectional dimension, wherein the third lumen and the fourth lumen comprise longitudinal axes that are located on the same half of the cross-sectional dimension of the flexible shaft.

C. The system of A or B, wherein the flexible shaft is a catheter portion, further comprising a cap portion, wherein the first, second, third and fourth lumens are included within the catheter portion, wherein at least a proximal end of the first orientation pin is received within the third lumen, wherein at least a proximal end of the second orientation pin is received within the fourth lumen, wherein the cap portion comprises: a first lumen; a second lumen; a third lumen; and a fourth lumen, wherein at least a distal end of the first orientation pin is received within the third lumen of the cap portion, wherein at least a distal end of the second orientation pin is received within the fourth lumen of the cap portion.

D. The system of C, wherein the first-fourth lumens of the catheter portion are aligned with the first-fourth lumens of the cap portion when the orientation pins are received within the third lumens and the fourth lumens of the catheter portion and the cap portion.

E. The system of D, wherein the cap portion further comprises: an exit port for exposing at least a portion of the second lumen of the cap portion; and a ramp located at a distal end of the second lumen of the cap portion.

F. The system of any of A-E, wherein the second lumens of the catheter portion and the cap portion are located on the same half of the cross-sectional dimension as the third and fourth lumens of the catheter portion and the cap portion.

G. The system of an of E or F, wherein the cap portion comprises one or more materials that are permeable to ultrasound signals, wherein the orientation pins comprise one or more materials that are non-permeable to ultrasound signals.

H. The system of any of A-G, wherein the orientation pins comprise at least one laser scribe, divot, hole, or other echogenic feature.

I. A catheter system comprising: a flexible shaft comprising: a first lumen; a second lumen; a first orientation pin; and a second orientation pin, a cap portion comprising: a first lumen; a second lumen; a third lumen; and a fourth lumen, wherein the first orientation pin is received within the third lumen of the cap portion, wherein the second orientation pin is received within the fourth lumen of the cap portion.

J. The system of I, further comprising a third orientation pin, wherein the cap portion further comprises a fifth lumen configured to receive the third orientation pin.

K. The system of I or J, wherein the orientation pins comprise at least one laser scribe, divot, hole, or other echogenic feature.

L. A system comprising: a radial ultrasound system comprising: a signal processor; and a radial ultrasound probe, wherein the radial ultrasound probe is in data communication with the signal processor, wherein the signal processor is configured to generate one or more images based on data received from the radial ultrasound probe; a display device configured to present the generated one or more images; a medical device; and a catheter system comprising: a catheter portion comprising: a first lumen configured to receive the radial ultrasound probe; and a second lumen configured to receive the medical device; a first orientation pin; a second orientation pin; and a cap portion comprising: a first lumen; a second lumen; a third lumen; and a fourth lumen, wherein the first orientation pin is received within the third lumen of the cap portion, wherein the second orientation pin is received within the fourth lumen of the cap portion.

M. The system of L, wherein the cap portion comprises a cross-sectional dimension, wherein the third lumen and the fourth lumen of the cap portion comprise longitudinal axes that are located on the same half of the cross-sectional dimension of the cap portion.

N. The system of L or M, wherein the cap portion further comprises: an exit port for exposing at least a portion of the second lumen of the cap portion; and a ramp located at a distal end of the second lumen of the cap portion.

O. The system of any of L-N, wherein the second lumens of the catheter portion and the cap portion are located on the same half of the cross-sectional dimension as the longitudinal axes of the third and fourth lumens of the cap portion.

P. The system of any of L-O, wherein the orientation pins comprise at least one laser scribe, divot, hole, or other echogenic feature.

The description of the invention is merely exemplary in nature and variations that do not depart from the gist of the invention are intended to be within the scope of the invention. Such variations are not to be regarded as a departure from the spirit and scope of the invention.

What is claimed is:

1. A catheter system comprising:
   a flexible shaft comprising:
   a first lumen;
   a second lumen;
   a third lumen;
   a fourth lumen;
   a first orientation pin; and
   a second orientation pin,
   wherein at least a proximal end of the first orientation pin is received within the third lumen of the flexible shaft,
   wherein at least a proximal end of the second orientation pin is received within the fourth lumen of the flexible shaft; and
   a cap portion comprising:
   a first lumen;
   a second lumen;
   a third lumen; and
   a fourth lumen,
   wherein at least a distal end of the first orientation pin is received within the third lumen of the cap portion,
   wherein at least a distal end of the second orientation pin is received within the fourth lumen of the cap portion.

2. The system of claim 1, wherein the flexible shaft comprises a cross-sectional dimension, wherein the third lumen and the fourth lumen comprise longitudinal axes that are located on the same half of the cross-sectional dimension of the flexible shaft.

3. The system of claim 1, wherein the first-fourth lumens of the catheter portion are aligned with the first fourth lumens of the cap portion when the orientation pins are received within the third lumens and the fourth lumens of the catheter portion and the cap portion.

4. The system of claim 3, wherein the cap portion further comprises:
   an exit port for exposing at least a portion of the second lumen of the cap portion; and
   a ramp located at a distal end of the second lumen of the cap portion.

5. The system of claim 3, wherein the second lumens of the catheter portion and the cap portion are located on the same half of the cross-sectional dimension as the third and fourth lumens of the catheter portion and the cap portion.

6. The system of claim 3, wherein the cap portion comprises one or more materials that are permeable to ultrasound signals, wherein the orientation pins comprise one or more materials that are non-permeable to ultrasound signals.

7. The system of claim 1, wherein the orientation pins comprise at least one laser scribe, divot, hole, or other echogenic feature.

8. A system comprising:
   a radial ultrasound system comprising:
      a signal processor; and
      a radial ultrasound probe,
      wherein the radial ultrasound probe is in data communication with the signal processor,
      wherein the signal processor is configured to generate one or more images based on data received from the radial ultrasound probe;
   a display device configured to present the generated one or more images;
   a medical device; and
   a catheter system comprising:
      a catheter portion comprising:
         a first lumen configured to receive the radial ultrasound probe; and
         a second lumen configured to receive the medical device;
      a first orientation pin;
      a second orientation pin; and
      a cap portion comprising:
         a first lumen;
         a second lumen;
         a third lumen; and
         a fourth lumen,
      wherein the first orientation pin is received within the third lumen of the cap portion,
      wherein the second orientation pin is received within the fourth lumen of the cap portion.

9. The system of claim 8, wherein the cap portion comprises a cross-sectional dimension, wherein the third lumen and the fourth lumen of the cap portion comprise longitudinal axes that are located on the same half of the cross-sectional dimension of the cap portion.

10. The system of claim 8, wherein the cap portion further comprises:
    an exit port for exposing at least a portion of the second lumen of the cap portion; and
    a ramp located at a distal end of the second lumen of the cap portion.

11. The system of claim 8, wherein the second lumens of the catheter portion and the cap portion are located on the same half of the cross-sectional dimension as the longitudinal axes of the third and fourth lumens of the cap portion.

12. The system of claim 8, wherein the orientation pins comprise at least one laser scribe, divot, hole, or other echogenic feature.

* * * * *